United States Patent
Miller et al.

(10) Patent No.: US 7,519,492 B2
(45) Date of Patent: Apr. 14, 2009

(54) APPARATUS AND METHOD FOR FULLY AUTOMATED CLOSED SYSTEM QUALITY CONTROL OF A SUBSTANCE

(75) Inventors: Peter Miller, New London, CT (US); Jan Henrik Ardenkjaer-Larsen, Frederiksberg C (DK); Martin John Bradney, Herefordshire (GB); Andrew Michael Leach, Clifton Park, NY (US); Per Christian Sontum, Oslo (NO); Eric John Telfeyan, Guilderland, NY (US); David Brandon Whitt, Albany, NY (US); Jan Wolber, Hertfordshire (GB)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/743,288

(22) Filed: May 2, 2007

(65) Prior Publication Data

US 2008/0275659 A1    Nov. 6, 2008

(51) Int. Cl.
*G01N 37/00* (2006.01)
*G06F 11/00* (2006.01)
(52) U.S. Cl. .............................. 702/84; 702/85; 702/86; 702/189; 700/9
(58) Field of Classification Search ............. 702/81–84, 702/188–192; 700/1, 2, 9; 356/364–370
See application file for complete search history.

(56) References Cited

U.S. PATENT DOCUMENTS

| 4,483,927 | A | * | 11/1984 | Takekawa ..................... 436/43 |
| 5,073,720 | A | | 12/1991 | Brown |
| 6,234,997 | B1 | | 5/2001 | Kamen et al. |
| 6,342,948 | B1 | | 1/2002 | Gilby |
| 6,466,814 | B1 | | 10/2002 | Ardenkjaer-Larsen et al. |
| 6,741,365 | B2 | * | 5/2004 | Curtis ......................... 356/627 |
| 2002/0001078 | A1 | | 1/2002 | Gobel et al. |
| 2006/0192559 | A1 | * | 8/2006 | Ardenkjaer-Larsen et al. ... 324/321 |
| 2007/0260491 | A1 | * | 11/2007 | Palmer et al. .................. 705/3 |

OTHER PUBLICATIONS

PCT Search Report—Sep. 3, 2008.

* cited by examiner

*Primary Examiner*—Eliseo Ramos Feliciano
*Assistant Examiner*—Phuong Huynh
(74) *Attorney, Agent, or Firm*—Eileen Walsh Gallagher (57) ABSTRACT

The present invention provides an apparatus and method for automated quality control of a substance comprising a compartment wherein a substance is located, a monitoring device coupled to the compartment and configured to monitor at least one quality control parameter prior to an end-use of the substance, and a processor coupled to the monitoring device, wherein the monitoring device is configured to communicate data to the processor for comparing at least one quality control parameter to an end-use value, and wherein the processor is further configured to control the release of the substance from the compartment to its end-use.

23 Claims, 5 Drawing Sheets

APPARATUS AND METHOD FOR FULLY AUTOMATED CLOSED SYSTEM QUALITY CONTROL OF A SUBSTANCE

BACKGROUND

This invention is directed to an apparatus and method for fully automated, noninvasive quality control of a substance in a closed system. More specifically, it relates to an apparatus and method for noninvasively measuring physical, chemical or optical properties of a substance, and comparing the measured values to end-use acceptable values for the substance.

Quality Control (hereinafter "QC") devices and methods have become an increasingly important part of healthcare over the last few decades. Typically, QC devices utilize invasive methods such as testing with probes, and/or substance withdrawal techniques to assess whether the substance meets its threshold guidelines. However, invasive techniques like the ones employed in many QC apparati are not suitable for applications that require a substance to be part of an entirely closed and sterile system, or where substance loss is undesirable.

Furthermore, specifically in healthcare, QC has traditionally occurred at the site of the manufacturer, as opposed to the point of use. However, with the development of new contrast agents and other short half-life pharmaceutical products, it may be necessary to perform compounding or processing steps immediately prior to administration into the patient. Prior to injection, the safety and efficacy of the substance must be ensured. A fully automated noninvasive QC analysis at this point of use would serve as an insurance.

The use of some noninvasive techniques to gather information about a particular substance is well known in the art. For instance, the use of absorption spectroscopy to find the concentration of known solutions is well known. Additionally, infrared pyrometery has been used to noninvasively measure the temperature of a substance.

Difficulties arise when QC of a substance requires testing multiple variables in real-time, when full automation is necessary. By "real-time" is meant that the results of the QC are produced at substantially the same rate that the data is acquired.

Such a QC apparatus, for example, may be useful in medicinal applications in which an agent is administered directly to a patient, where it may be necessary to ensure the efficacy and safety of the pharmaceutical product being tested by acquiring, for instance, the pH, temperature, liquid-state polarization, concentration and/or volume of the agent while comparing those values to proper end-use values or threshold guidelines, all without the substance leaving a closed system. In addition, such a QC system may operate directly at a patient's bedside, potentially obviating the need of a bedside pharmacist.

Therefore, what is needed is a fully automated, noninvasive, closed system QC apparatus and method adapted to measure one or more properties of a substance in real-time, compare each property value to an appropriate end-use value, and if the substance meets the end-use value, a release mechanism configured to allow for the release of the substance to its end-use all while preserving the sterility of the substance being tested.

BRIEF DESCRIPTION

In a first aspect, the invention provides an apparatus for fully automated, closed system quality control of a substance comprising a compartment wherein a substance is located, a monitoring device coupled to the compartment and configured to monitor at least one quality control parameter prior to an end-use of the substance, and a processor coupled to the monitoring device, wherein the monitoring device is configured to communicate data to the processor for comparing at least one quality control parameter to an end-use value, and wherein the processor is further configured to control the release of the substance from the compartment to its end-use.

In a second aspect, the invention provides a method for fully automated, closed system quality control comprising monitoring a substance in a compartment for an at least one quality control parameter prior to an end-use of the substance, processing data received from the monitoring device, wherein the processor is configured to calculate and compare at least one quality control parameter with an end-use value and releasing the substance from the compartment to its end-use if the at least one quality control parameters meets the end-use value.

Also, provided in a third aspect, the invention provides an executable method for processing quality control substance data comprising a computer readable program that is capable of storing substance data and comparing the stored substance data to data received from a monitoring device, wherein the computer readable program is configured to calculate an at least one quality control parameter and has a storage data disc for storing data on a storage medium.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following detailed description is exemplary and not intended to limit the invention of the application and uses of the invention. Furthermore, there is no intention to be limited by any theory presented in the preceding background of the invention or the following detailed description of the drawings.

While this invention is particularly directed to the art of fully automated non-invasive QC, it will be appreciated that the invention may have usefulness in other fields. For example, the invention will also find useful application in a wide range of environments where non-invasive and comprehensive measurements of physical, chemical and thermal properties is desired.

As used herein, "adapted to," "coupled," and the like refer to mechanical, structural or optical connections between elements to allow the elements to cooperate to provide a described effect.

In a first embodiment, the invention provides an apparatus for fully automated, closed system quality control of a substance comprising a compartment wherein a substance is located, a monitoring device coupled to the compartment and configured to monitor at least one quality control parameter (e.g., temperature, volume, pH, concentration, or any combination thereof) prior to an end-use of the substance, and a processor coupled to the monitoring device, wherein the monitoring device is configured to communicate data to the processor for comparing at least one quality control parameter to an end-use value, and wherein the processor is further configured to control the release of the substance from the compartment to its end-use. As used herein, the term "compartment" refers to an apparatus that is configured to hold a sterile vessel where the substance being tested actually resides. For example, the compartment may cradle the sterile vessel, while ensuring the alignment of all measurement components of the QC apparatus. In addition, the vessel will ensure that the substance does not come into direct contact with QC device, thereby further ensuring the sterility of the substance path. The sterile vessel may then be discarded after use.

The monitoring device may comprise a plurality of devices configured to collect data about the substance in the compartment which may include an at least first light source that is configured to transmit light through an at least first dimension of the compartment, and an at least first light-receiving device that is coupled to the processor, and that receives light from the at least first light source. Furthermore, the QC device may provide a release mechanism (e.g. needle and septum, a valve, a tap, a hatch, a physical barrier, or any combination thereof) coupled to the processor, wherein the processor is configured to command the release mechanism to allow a substance to its end-use if an acceptable end-use value is obtained. Additionally, this embodiment may also comprise an initiatory procedure wherein an operator instructs the apparatus to begin quality control analysis.

In a second embodiment, the invention provides a method for fully automated, closed system quality control comprising monitoring the substance in a compartment for an at least one quality control parameter prior to an end-use of the substance, processing data received from the monitoring device, wherein the processor is configured to calculate and compare at least one quality control parameter (e.g., substance identification, temperature, volume, pH, concentration, liquid-state polarization, or any combination thereof) with an end-use value, and releasing the substance from the compartment to its end-use if the at least one quality control parameters meets the end-use value. The monitoring step may comprise transmitting light through at least one dimension of the compartment, and detecting the transmitted light from the at least one dimension of the compartment, wherein the monitoring device may be further configured to transmit data to a processor. The processing step may comprise calculating at least one quality control parameter and comparing the at least one quality control parameter to an at least one end-use value, and the releasing step may comprise a needle and septum, wherein the needle is configured to pierce the compartment and release the substance to its end-use if an at least one quality control value meets an end-use value (or may also comprise a valve, a tap, a hatch or any combination thereof).

Furthermore, the method may also comprise an initiation step, wherein an operator may manually begin QC process (e.g., push-button initiation).

In a third embodiment, the invention provides an executable method for processing quality control substance data comprising a computer readable program that is capable of storing substance data and comparing the stored substance data to data received from a monitoring device, wherein the computer readable program is configured to calculate an at least one quality control parameter, and has a storage data disc for storing data on a storage medium.

Figure 1:
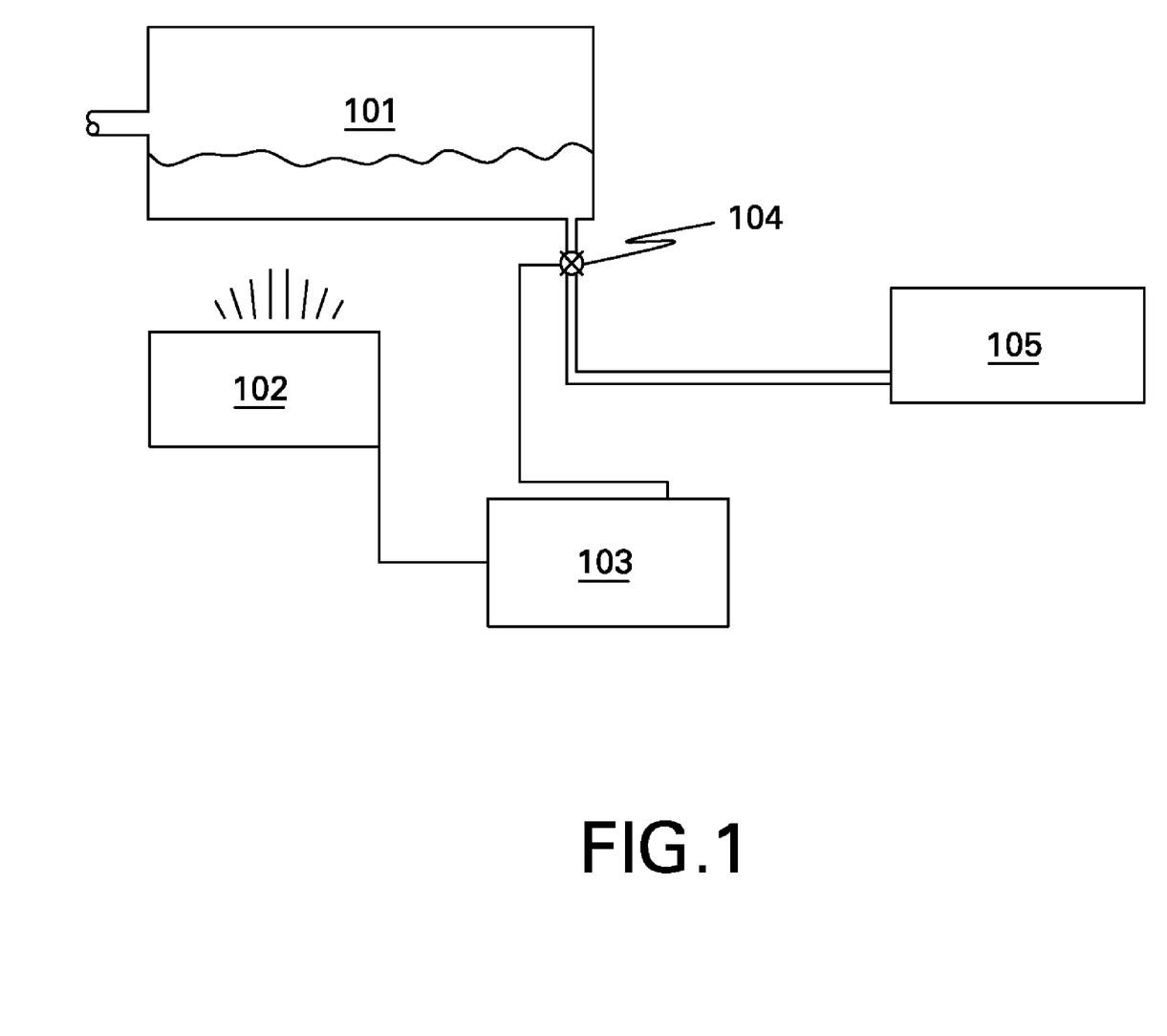
FIG. 1 is a block diagram of a QC device to which embodiments of the present invention are applicable.

Referring to FIG. 1, there is shown a block diagram of a QC apparatus for which embodiments of the present invention are applicable. The QC apparatus comprises a compartment 101, in which a substance may be collected. As used herein, the term "substance" may comprise any liquid or gas. However, the term "substance" may also comprise liquid crystal, colloidal dispersions, plasmas, solid suspensions, amorphous solids, or any combination thereof. For automated QC of a substance in the compartment 101, a monitoring device 102 is coupled to the compartment 101 and is configured to gather optical, thermal, physical, electrical, magnetic and/or chemical information about the substance. The processor 103 is coupled (e.g., optically, electrically, magnetically, mechanically) to the monitoring device 102, and is configured to receive data from the monitoring device 102. The processor 103 is further configured to perform a comparative analysis on the substance in the compartment 101. A comparative analysis comprises computing applicable QC values, including but not limited to substance identity, concentration, pH, volume, liquid-state polarization, and temperature and comparing at least one QC value against an at least one end-use acceptable value. A release mechanism 104 may function with the compartment 101 to allow for the release of the substance, the release mechanism 104 being further coupled the processor 103. The processor 103 may be further configured to transmit a signal to a release mechanism 104, wherein the release mechanism 104 may release the substance from the compartment 101 to its end-use 105 when a set of one or more end-use acceptable values is obtained. As used herein, "QC value," "QC parameter" and the like refers to any property of a substance that may be the subject of testing e.g., temperature, pH, volume, concentration, liquid-state polarization, density, identity, mass, etc. As used herein, "end-use acceptable value," "end-use value" and the like refers to a specific value e.g. 100° C., 100 mL, any range of values e.g. 100-110° C., 100-110 mL or an upper or lower bound e.g. greater than 100° C., or less than 100 mL.

The compartment 101 may be any of any useful shape or size. In an embodiment of the present invention, the compartment 101 is rectangular in shape, and is designed to cradle a sterile vessel wherein a substance resides, wherein the compartment is further designed to ensure the alignment of measurement components of the present invention. However, in other embodiments the compartment may be spherical or conical in shape, again wherein the compartment is designed to cradle a matching (i.e., in size and shape) sterile vessel and align the present inventions measurement components. Furthermore, in accordance with embodiments of the present invention, the compartment 101 may be assembled with a transparent material, or may contain at least two parallel or opposing windows transparent to one or more wavelengths of light. For example, the monitoring device 102 may transmit light through one window of the compartment 101, and may detect the light transmitted through a parallel window. If, however, the compartment is made entirely of transparent material, the monitoring device 102 may transmit light through one side of the compartment 101 and detect it on a parallel side. If fluorescence is used, detection of light may occur at alternative angles (e.g., 90° or 180°) of the compartment. Additionally, in more specific embodiments, the compartment 101 may be composed entirely of a low thermal mass material, such as thin glasses or plastics (e.g. polymethyl methacrylate, polycarbonate, polystyrene, quartz, etc.) to allow for more accurate noninvasive temperature measurement, which will be discussed in greater detail with reference to FIG. 2.

Figure 2:
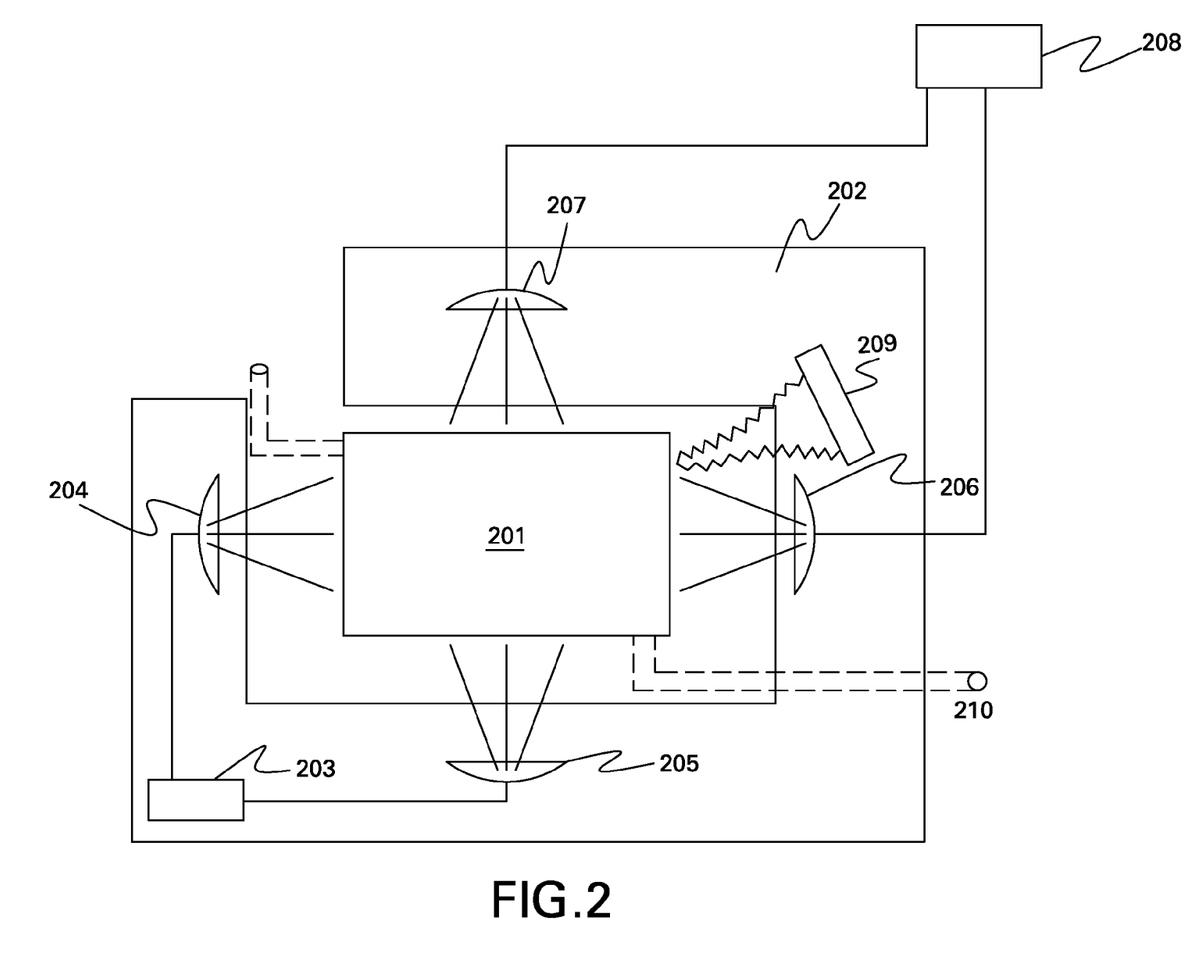
FIG. 2 is a more detailed block diagram depicting an exemplary embodiment of a QC device, and further depicting exemplary elements of the monitoring device.

In embodiments of the present invention, monitoring device 102 may comprise a plurality of devices, each functioning in either a separate capacity or in conjunction with one another to measure the intrinsic properties of a substance. With reference to FIG. 2, an exemplary embodiment of a monitoring device 202 is shown, which may be configured to gather data about the substance in compartment 201, and may be further configured to transmit the data to the processor 208. The processor 208, using the information received from the monitoring device 202, may be configured to calculate chosen QC values (e.g., pH, volume, temperature, concentration, liquid-state polarization, etc.) and run a comparative analysis.

In the embodiment shown in FIG. 2, monitoring device 202 comprises one or more of a plurality of devices located within the monitoring device. In one exemplary embodiment, monitoring device 202 comprises a first light source 203 that may be fiber optics based, to allow for measurements to be taken from different dimensions of the compartment 201. For instance, light source 203 may be connected fiber optically to light transmitter 204 and 205, wherein each light transmitter may be configured to transmit light through a first and second dimension of the compartment 201. As used herein, the term "light transmitter" refers to the point and location at which light from the fiber optic connection is transmitted at the compartment. In this particular embodiment, light transmitter 204 may transmit light through the x-axis of the compartment 201 and light transmitter 205 may transmit light through the y-axis of the compartment 201. Alternatively, two separate light sources may also be used to transmit light, each positioned on different dimensions of the compartment 201. In this particular embodiment, light sources are themselves light transmitters as well. The at least one light source 203 may also comprise light emitting diodes (LEDs), lasers, halogen or deuterium lamps, etc.

Referring further to FIG. 2, a first light detector 206 and a second light detector 207 may be positioned to detect the light transmitted from light transmitters 204 and 205 respectively, after the light passes through compartment 201. For example, light detector 207 may be positioned to detect light from light transmitter 205 on the y-axis, and light detector 206 may be positioned to detect light from light transmitter 204 on the x-axis of the compartment 201. Light detectors 206 and 207 are coupled, e.g. electronically, to processor 208, and communicate optical, thermal, physical, and/or chemical data gathered about the substances to the processor 208. Light detecting devices may comprise fiber optic detectors as part of a fiber optic spectrometer system, spectrophotometers, infrared emission detectors, photodetectors, cameras (CCD, CMOS), etc.

Additionally, monitoring device 202 may be configured to gather thermal information about a substance. Referring again to FIG. 2, the monitoring device 202 may comprise an infrared emission detector 209 (e.g., fixed-mount optical or infrared pyrometer) configured to measure the temperature of the substance in the compartment 201. The infrared emission detector 209 may be coupled to the processor 208, and may be configured to communicate thermal data about the substance to the processor 208. In an exemplary embodiment, an infrared pyrometer 209 is provided as part of monitoring device 202 and the pyrometer is positioned at a functional distance from the compartment 201 on any side of the compartment 201.

The processor 208 may be further configured to measure the volume of the substance in the compartment by utilizing information gathered from the first and second light-detecting device 206 and 207. In this embodiment, the substance may itself be optically active or may contain an optically active species, e.g., a chromophore. One dimension of the compartment 201 is a known path-length, while a second dimension, corresponding directly or indirectly to fluid level, is an unknown path-length. By utilizing optical relationships, commonly known to one skilled in the art, the unknown path-length of the second dimension, and therefore the fluid level and volume of the substance can be calculated. Furthermore, the optical properties utilized in this invention may include, but are not limited to absorbance, scatter, and changes of refractive index.

Referring again to FIG. 2, the processor 208 may be further adapted to calculate the pH of the substance in the compartment 201 by utilizing information gathered from the monitoring device 202. In one embodiment, the processor 208 utilizes ultraviolet absorbance (herein after UV absorbance) to calculate pH, based on the observation that the absorbance spectrum for a given substance is pH dependant. This technique comprises producing a mathematical model correlating pH to the absorbance spectra of a substance X at one or more wavelengths, and loading the information into the processor 208. The processor 208 may then compare UV absorbance data gathered from the monitoring device and use the above referenced mathematical model to back-calculate the pH of the substance. Alternatively, the monitoring device 202 may utilize fluorescence spectroscopy to determine pH, which is well known in the art.

Referring again back to FIG. 2, processor 208 may be further adapted to calculate substance concentration of the substance in the compartment 201. In an embodiment of the present invention, the processor 208 utilizes information gathered by light detecting devices 206 and 207 and uses UV/vis spectrophotometer techniques to measure the UV absorbance of the substance in the compartment 201. The processor 208 may be preloaded with calibration curves at appropriate wavelengths for a chosen substance, and may be configured to calculate substance concentration using the UV absorbance and the preloaded calibration data.

The processor 208 may be further adapted to identify the substance in the compartment 201. Two exemplary techniques, which may be employed separately or in tandem, include UV-Vis spectroscopy, and/or IR absorbance spectroscopy. In an embodiment of the present invention, the processor 208 may be preloaded with UV-Vis absorbance spectra and/or IR absorbance spectra for a plurality of substances that may be subject to QC analysis. Processor 208 may then utilize optical data from monitoring device 202, and perform a statistical comparative analysis, matching the information to preloaded UV or IR spectra to determine substance identity.

The processor 208 may be further adapted to measure the degree of liquid-state polarization. In an embodiment of the present invention, block 209 may comprise a polarimeter adapted to measure the liquid-state polarization of a substance. The polarimeter may further be configured to communicate the data to the processor 208 wherein the data may be compared to acceptable end-use values.

Figure 3:
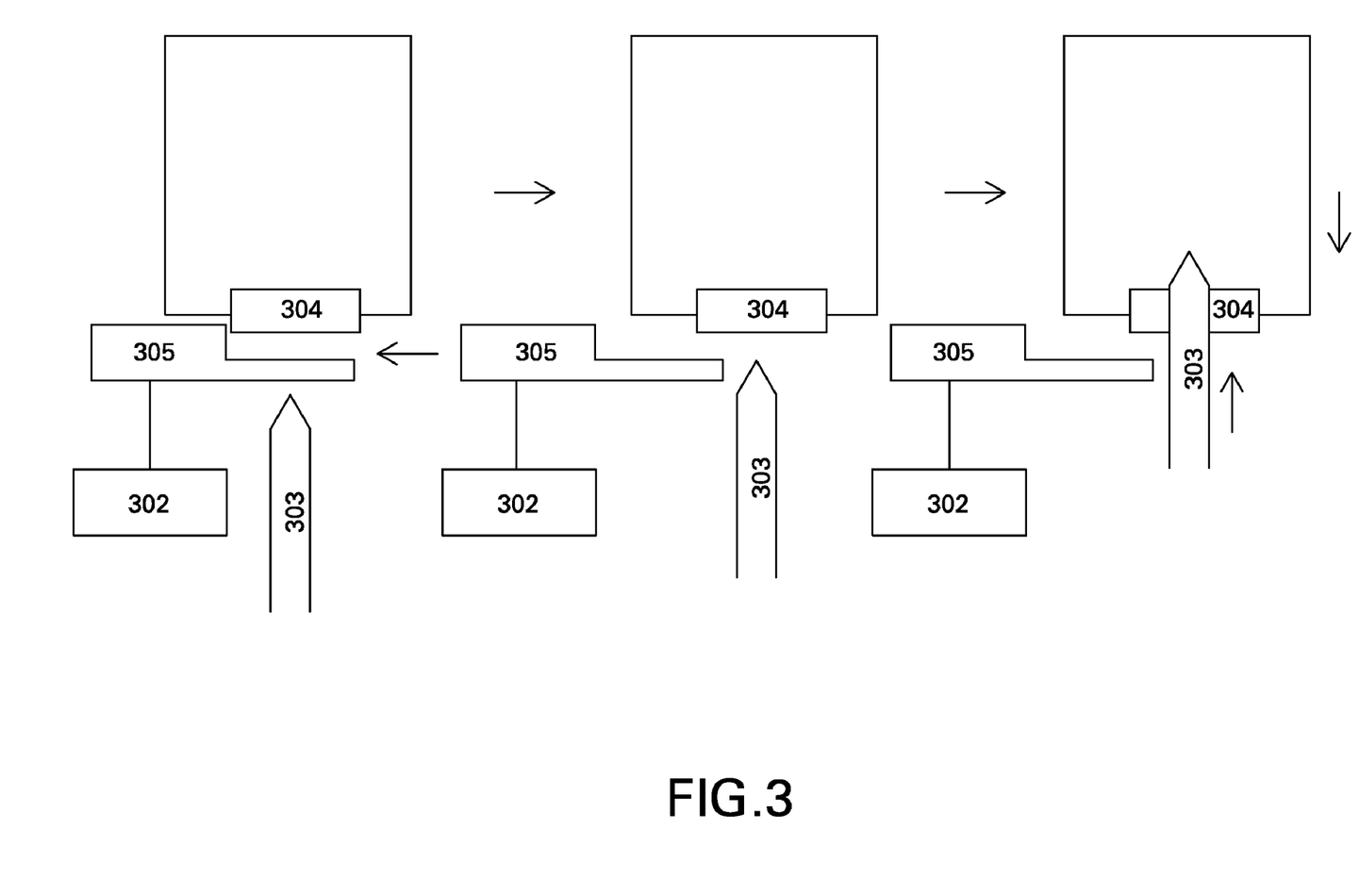
FIG. 3 depicts an exemplary embodiment of a release mechanism comprising a physical barrier and a needle and septum, wherein the physical barrier is configured to allow the needle to pierce the compartment to release the substance if appropriate QC values are obtained.

Referring to FIG. 3, an embodiment for controlling the release of a substance is shown. The processor 302 is coupled to physical barrier 305 which functions to release the substance to its end-use. The exemplary release mechanism shown in FIG. 3 comprises a physical barrier 305, a needle 303 and septum 304. In this particular exemplary embodiment, the processor 302 may be configured to signal the removal of the physical barrier 305, wherein an operator may then inject the needle 303 into the compartment 301, therein permitting the release of the substance to its end-use when one or more end-use acceptable QC values are obtained. Conversely, if the selected values for the chosen properties do not meet the chosen end-use value(s), the processor 302 will not signal the removal of the physical barrier, thereby insuring that if the substance does not pass QC, an operator will not able to inject the needle 303 through the septum 304, and the substance will be incapable of being released to its end-use. The operator may have the ability to select which values, and for which properties e.g., pH, concentration, volume, etc. the processor 302 may evaluate before the physical barrier is removed. As used herein "operator" refers to a person, for example a clinician, who may in some embodiments of the present invention choose QC properties and values for the QC apparatus to test. In other embodiments, the clinician merely initiates the process, and has no control over the QC apparatus post-initiation. In this particular embodiment, the QC properties and values may be pre-set, for example by a manufacturer or other qualified person, because it may be preferable for QC properties and values to be inaccessible to the operator thereby lessening the probability of operator error.

Generally, either the substance passes all of the appropriate QC tests and is released from the compartment 301, or it fails one or more tests and is not released. It is to be appreciated that the release mechanism may also comprise a valve, a hatch, a tap, a spigot, mechanical needles or levers, restraining arms or bars, etc. Naturally, an operator may be used to initiate the process in any embodiment, e.g., by pressing a button or issuing a start command to the QC apparatus.

Figure 4:
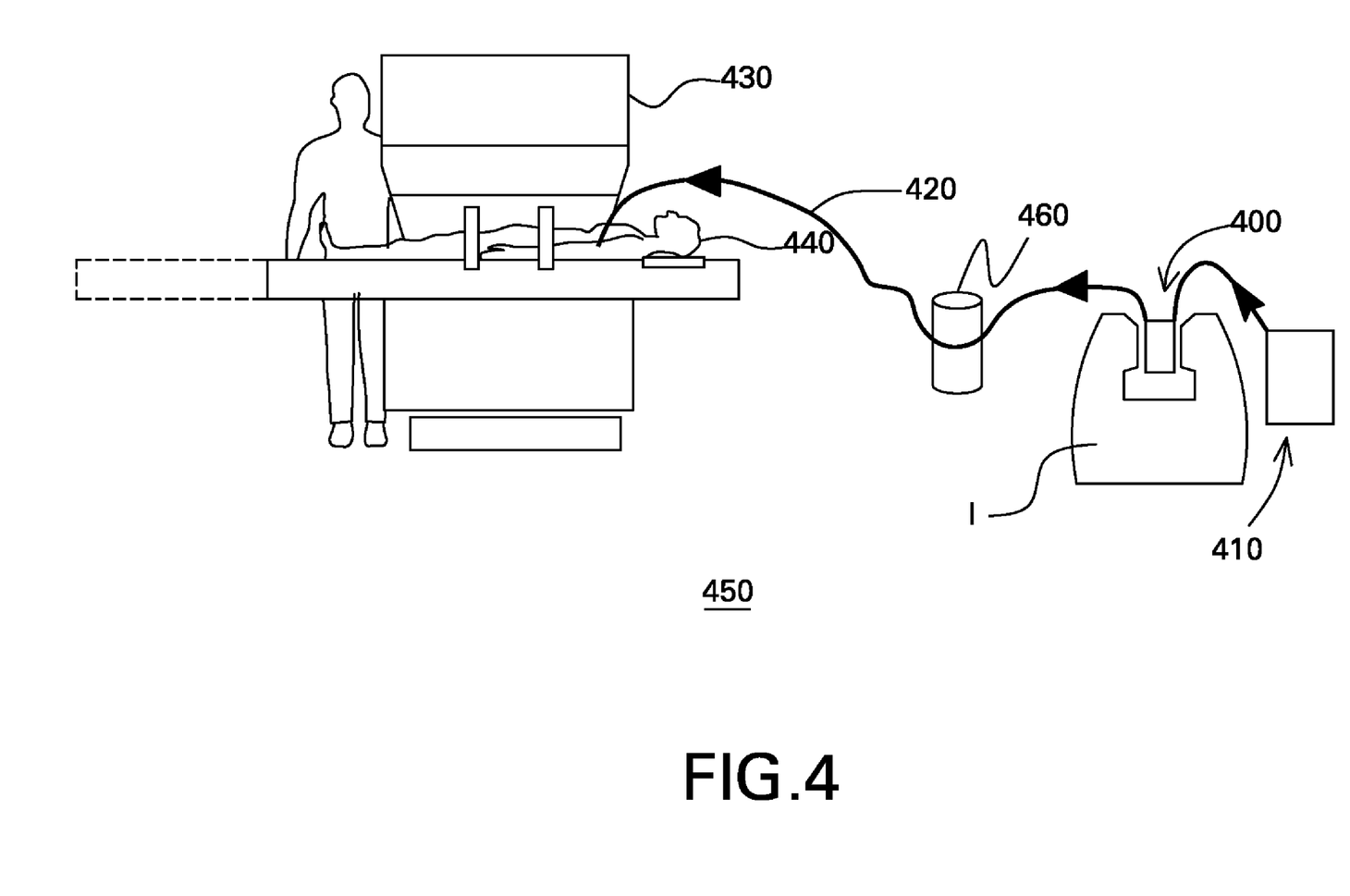
FIG. 4 is an illustration of an exemplary MRI system and polarizing subsystem for which embodiments of the present invention are applicable.

FIG. 4 is an illustration of an exemplary MRI system and polarizing subsystem for which embodiments of the present invention may be applicable.

Referring to FIG. 4, a exemplary system 450 is shown for producing hyperpolarized samples for use in a MRI device and includes a cryostat 1 and polarizing subsystem 400 for processing material from container 410 and resulting in the hyperpolarized material. A material delivery line 420 is used to deliver the hyperpolarized material to subject 440 within MRI scanner 430. In the embodiment shown in FIG. 4, the hyperpolarized samples are used in an in vivo imaging application, where the hyperpolarized samples must undergo automated QC analysis in compartment 460 to ensure that proper efficacy and safety standards are met before the product is released for patient delivery through line 420.

Referring further to FIG. 4, container 410 contains a solid sample of the sample to be polarized can be polarized while still in the solid phase by any appropriate known method, e.g. brute force polarization, dynamic nuclear polarization or the spin refrigerator method, while being maintained at a low temperature (e.g. under 100 K) in a strong magnetic field (e.g. 1-25 T). After the solid sample has been polarized, it is melted or dissolved with a minimum loss of polarization. In the following the expression "melting means" will be considered to mean the following: a device, e.g. a heated solvent, capable of providing sufficient energy to the solid polarized sample to melt it or otherwise bring the polarized sample into solution for introduction into the subject being imaged. As used herein, the term "solid" refers to solid materials, semi-solid materials or any combination thereof provided the material requires some transformation to attain a liquid-state suitable for introduction into a subject being imaged.

When the polarized material is in its liquid-state, held in polarized sub-system 460, embodiments of the present invention are applicable. In an exemplary embodiment, substance $^{13}C$ pyruvate in polarized form is the substance to be used during in vivo imaging, and is therefore also the substance subject to QC analysis, which may take place in compartment 460 of the polarized subsystem.

In this exemplary embodiment, the QC method comprises monitoring the $^{13}C$ pyruvate (hereinafter the "pyruvate solution") for at least one QC parameter, processing the data, wherein the processor may be configured to calculate and compare to at least one QC parameter with an end-use value, and if the QC value meets the end-use value, releasing the pyruvate solution into the patient prior to imaging. In this particular embodiment QC parameters may include substance identification, and pH, volume, and temperature measurement, polarization, and concentration.

Figure 5:
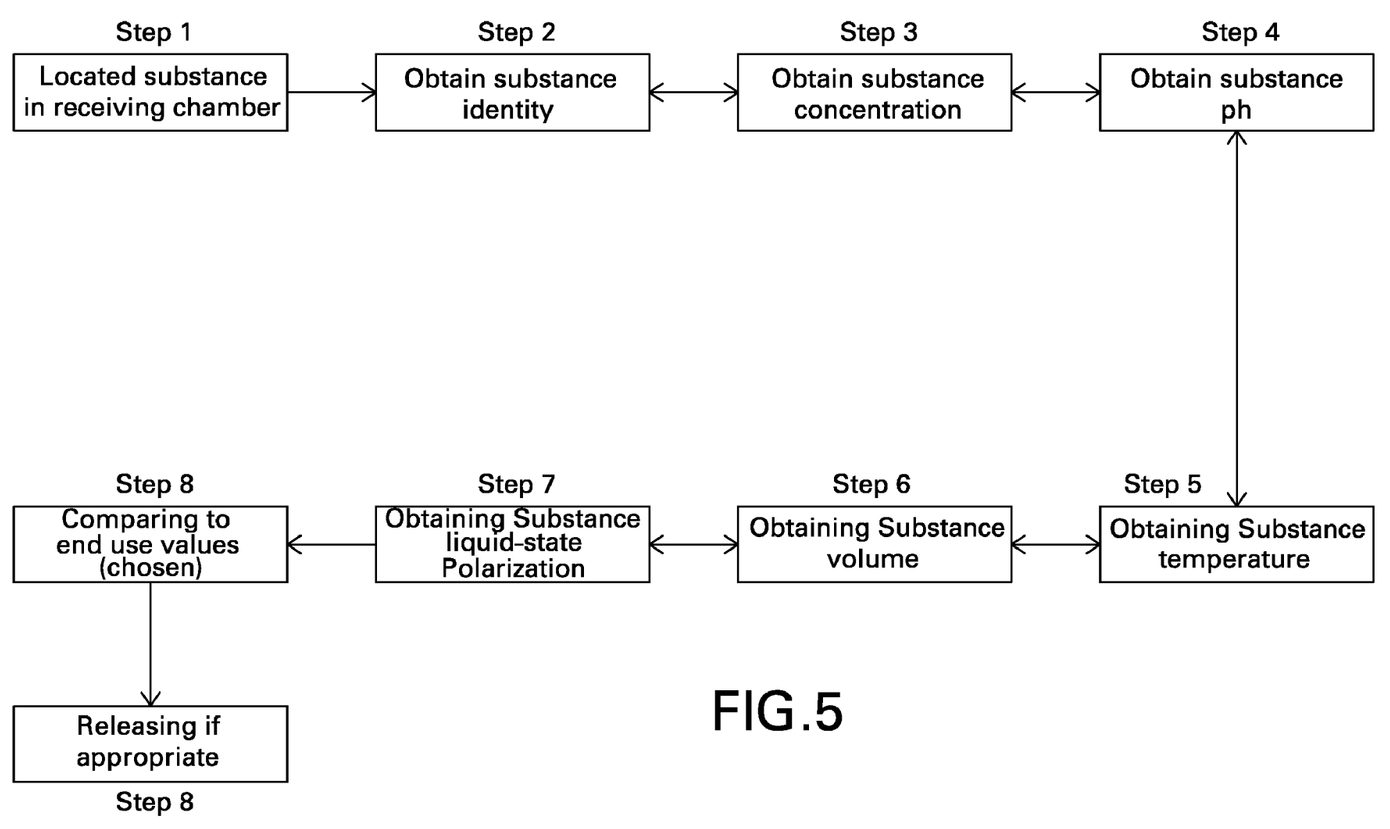
FIG. 5 is a flow chart illustrating one exemplary method by which the QC analysis takes place.

FIG. 5 is a flow chart illustrating one exemplary method by which the QC analysis takes place. Each step is described in further detail below. It is to be appreciated that each step may occur substantially concurrently, therefore significantly decreasing analysis time.

In step 1, pyruvate solution resides in a sterile vessel, which is located in the compartment after dissolution. Referring back to FIG. 4, the solution is located in compartment 460.

In step 2 of FIG. 5, measuring selected properties of the pyruvate solution in real-time begins. The processor may identify the substance as pyruvate using, for instance, UV absorbance data. The identification step comprises correlating the known spectral data for pyruvate with the data received from the light detecting devices to identify substances. In this example pyruvate may be identified.

In step 3 of FIG. 5, the concentration of a substance may be found using UV-Vis absorbance spectra. In this particular example, obtaining substance concentration comprises producing calibration curves for pyruvate at about at least one wavelength and loading the data into the processor. Next, by correlating this known data with the data received from the monitoring device, the processor may calculate pyruvate concentration.

In step 4 of FIG. 5, the pH of a substance may be found using UV-Vis absorbance spectra. In accordance with this step, the method comprises producing UV-Vis absorbance spectra at different pH's and equivalent concentrations. Using the shift at representative pHs, an embodiment for a method to measure pH may comprise creating a mathematical model that is used to accurately predict the pH of the pyruvate solution in the compartment by correlating model data with the information received from the monitoring device. Alternatively, fluorescence spectroscopy may be used to find the pH of the pyruvate solution.

In step 5 of FIG. 5, the temperature of the substance may be found using IR pyrometery. The step may comprise using a pyrometer to measure the IR emission of the solution by placing an infrared pyrometer at an applicable distance from the compartment. Because compartment material, wall thickness and emissivity are factors in pyrometer accuracy, the compartment may be constructed from thin, low thermal mass glasses or plastics such as polymethyl methacrylate, polycarbonate, or polystyrene. Alternatively, the compartment may comprise a window or wall constructed from thin low thermal mass glasses or plastics.

In step 6 of FIG. 5, the volume of a substance may be found using dual path-length absorbance. In this exemplary embodiment, the pyruvate solution is held in a rectangular compartment, and the pyruvate solution is itself optically active. Therefore no chromophore is needed as an addition to the pyruvate solution. The method comprises finding an unknown pathlength, corresponding directly or indirectly to pyruvate solution volume in the compartment using optical relationships commonly known to one skilled in the art. For example, referring back to FIG. 2, one dimension of the compartment 201 is a known path-length, while a second dimension, corresponding directly or indirectly to fluid level, is an unknown path-length. Using techniques well known in the art, the volume can be found by finding the unknown pathlength.

In step 7 of FIG. 5, the degree of liquid-state polarization may be found using a polarimeter placed at an appropriate distance from the compartment. The polarimeter may be further configured to communicate the data to the processor.

In step 8 of FIG. 5, the processor may compare operator chosen end-use values to the processor-calculated QC values, calculated at various steps described above. For example, in one particular exemplary embodiment, the operator (or any other qualified person) may input or chose values as acceptable end-use ranges for concentration, pH, temperature, degree of liquid-state polarization, and volume. If these ranges are obtained, the processor sends a signal to the release mechanism releasing the pyruvate solution into the patient for imaging, step 9.

Although the preceding example is a medicinal use, this invention may be applicable in industrial uses, such as assembly lines and food processing, pharmacological uses, or any instance where material loss is undesirable.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. An apparatus for fully automated closed system quality control of a hyperpolarized contrast agent comprising:
   a cryostat;
   a polarizer contained within the cryostat and configured to hyperpolarize a contrast agent;
   a material delivery line in fluid communication with the polarizer and configured to transport the hyperpolarized contrast agent from the polarizer;
   at least one compartment, outside the cryostat, capable of maintaining sterility of the hyperbolized contrast agent, in fluid communication with the material delivery line, and configured to receive the hyperpolarized contrast agent from the polizer;
   a monitoring device coupled to the compartment and configured to monitor at least one quality control parameter prior to an end-use of the hyperpolarized contrast agent and wherein the sterility of the hyperpolarized contrast agent is maintained during monitoring; and
   a processor coupled to the monitoring device, wherein the monitoring device is configured to communicate data to the processor for comparing at least one quality control parameter to an end-use value, and wherein the processor is further configured to control the release of the hyperpolarized contrast agent from the compartment to its end-use.

2. The apparatus of claim 1, wherein the monitoring device comprises a plurality of devices configured to collect data about the hyperpolarized contrast agent in the compartment.

3. The apparatus of claim 1, wherein the monitoring device comprises an at least first light source that is configured to transmit light through an at least first dimension of the compartment.

4. The apparatus of claim 1, wherein the monitoring device further comprises an at least first light-receiving device that is coupled to the processor, and that receives light from an at least first light source.

5. The apparatus of claim 1, wherein the at least first light source is a fiber optic system comprising an at least first optical cable configured to transmit light through an at least first dimension of the compartment.

6. The apparatus of claim 1, wherein the at least first light source comprises a light emitting diode, halogen lamp, tungsten lamp, or any combination thereof.

7. The apparatus of claim 1, wherein the at least first light detecting device is a fiber optic system comprising an at least first optical cable configured to detect light through an at least first dimension of the compartment, and wherein the at least first optical cable is further coupled to the processor.

8. The apparatus of claim 1, further comprising a release mechanism coupled to the processor, wherein the processor is configured to command the release mechanism to allow the hyperpolarized contrast agent to its end-use when an acceptable end-use value is obtained.

9. The apparatus of claim 1, wherein the release mechanism comprises a mechanical barrier, needle and septum, a valve, a tap, a hatch, or any combination thereof.

10. The apparatus of claim 1, wherein the at least one quality control parameter comprises measuring at least one of temperature, volume, pH, concentration, liquid-state polarization, or any combination thereof.

11. The apparatus of claim 1, wherein the processor is further configured to identify the hyperpolarized contrast agent in the compartment.

12. The apparatus of claim 1, wherein the processor further comprises memory configured to store information about an at least one hyperpolarized contrast agent.

13. The apparatus of claim 1, further comprising a sterile vessel wherein a hyperpolarized contrast agent resides, which is functionally adapted to fit into the at least one compartment, wherein the sterile vessel and the at least one compartment are aligned to facilitate measurements of the hyperpolarized contrast agent.

14. The apparatus of claim 1, further comprising an initiatory procedure wherein an operator instructs the apparatus to begin quality control analysis.

15. A method for fully automated closed system quality control of a hyperpolarized contrast agent comprising:
   hyperpolarizing a contrast agent in a polarizer contained within a cryostat;
   transferring the hyperpolarized contrast agent from the polarizer to a compartment, outside the cryostat, wherein the compartment is capable of maintaining the sterility of the hyperpolarized contrast agent;
   monitoring the hyperpolarized contrast agent in the compartment for an at least one quality control parameter prior to an end-use of the hyperpolarized contrast agent and wherein the sterility of the hyperpolarized contrast agent is maintained during monitoring;
   processing data received from the monitoring device, wherein a processor, in communication with the monitoring device, is configured to calculate and compare at least one quality control parameter with an end-use value; and releasing the hyperpolarized contrast agent from the compartment to its end-use when the at least one quality control parameters meets the end-use value.

16. The method of claim 15, wherein the monitoring step comprises transmitting light through at least one dimension of the compartment.

17. The method of claim 15, wherein the monitoring step further comprises detecting the transmitted light from the at least one dimension of the compartment, and wherein the monitoring device is further configured to transmit data to a processor.

18. The method of claim 15, wherein the processing step comprises calculating at least one quality control parameter and comparing the at least one quality control parameter to an at least one end-use value.

19. The method of claim 15, wherein the releasing step comprises a physical barrier and a needle, wherein the physical barrier is configured to allow the needle to pierce the compartment and release the hyperpolarized contrast agent to its end-use if at an least one quality control value meets an end-use value.

20. The method of claim 15, wherein the releasing step may further comprise a valve, a tap, a hatch, a spigot or any combination thereof.

21. The method of claim 15, wherein the at least one quality control parameter comprises hyperpolarized contrast agent identification, temperature, volume, pH, concentration, liquid-state polarization, or any combination thereof.

22. The method of claim 15, wherein the processing step further comprises providing memory for storage of data regarding at least one hyperpolarized contrast agent.

23. The method of claim 15, further comprising an initiation step, wherein an operator may manually initiate the quality control process.

* * * * *

UNITED STATES PATENT AND TRADEMARK OFFICE
CERTIFICATE OF CORRECTION

PATENT NO. : 7,519,492 B2  
APPLICATION NO. : 11/743288  
DATED : April 14, 2009  
INVENTOR(S) : Miller et al.

Page 1 of 1

It is certified that error appears in the above-identified patent and that said Letters Patent is hereby corrected as shown below:

In Column 9, Line 49, in Claim 1, delete "hyperbolized" and insert -- hyperpolarized --, therefor.

In Column 9, Line 52, in Claim 1, delete "polizer;" and insert -- polarizer; --, therefor.

In Column 12, Line 2, in Claim 19, delete "at an" and insert -- an at --, therefor.

Signed and Sealed this

Twenty-fifth Day of August, 2009

David J. Kappos
*Director of the United States Patent and Trademark Office*